United States Patent [19]

Taylor et al.

[11] Patent Number: 4,576,667

[45] Date of Patent: Mar. 18, 1986

[54] PROCESS FOR PREPARING A SINTERED CERAMIC ARTICLE WITH POROUS REGION

[75] Inventors: Dale F. Taylor, Schenectady; Louis S. Sammler, Clifton Park, both of N.Y.

[73] Assignee: General Electric Company, Schenectady, N.Y.

[21] Appl. No.: 656,566

[22] Filed: Oct. 1, 1984

Related U.S. Application Data

[62] Division of Ser. No. 451,501, Dec. 20, 1982, Pat. No. 4,560,413.

[51] Int. Cl.$^4$ .............................................. C03B 29/00
[52] U.S. Cl. ...................................... 156/89; 156/250; 156/294; 264/43; 264/66; 264/248
[58] Field of Search ................. 156/89, 250, 293, 294; 501/103, 104, 105; 264/43, 65, 66, 248

[56] References Cited

U.S. PATENT DOCUMENTS

| | | | |
|---|---|---|---|
| 3,239,323 | 3/1966 | Folweiler | 156/89 |
| 3,429,962 | 2/1969 | Krystyniak | 264/309 |
| 3,564,328 | 2/1971 | Bagley et al. | 156/89 |
| 4,264,424 | 4/1981 | Neidrach | 204/421 |
| 4,396,445 | 8/1983 | Sasaki et al. | 156/89 |

OTHER PUBLICATIONS

J. Electrochem. Soc., vol. 119, p. 39 (1972), Vermilyea and Indig.

Primary Examiner—Jay H. Woo
Assistant Examiner—Timothy W. Heitbrink
Attorney, Agent, or Firm—James Magee, Jr.; James C. Davis, Jr.

[57] ABSTRACT

A sintered metallic oxide article is disclosed comprising a non-porous body having at least one porous region formed therein in the general shape of a hollow cylinder, said region placing opposite sides of the body in flow communication. A method is set forth for producing the porous region with a preselected effective open cross-sectional area.

3 Claims, 2 Drawing Figures

U.S. Patent     Mar. 18, 1986     4,576,667
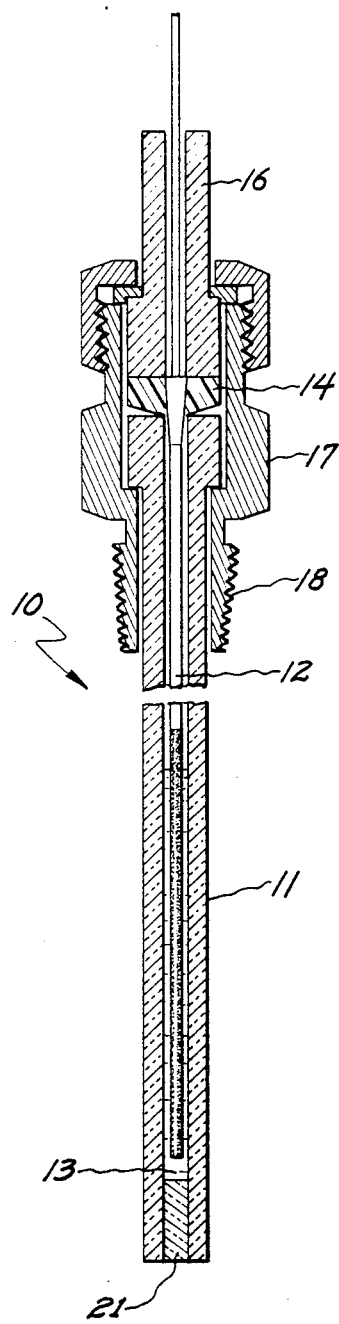
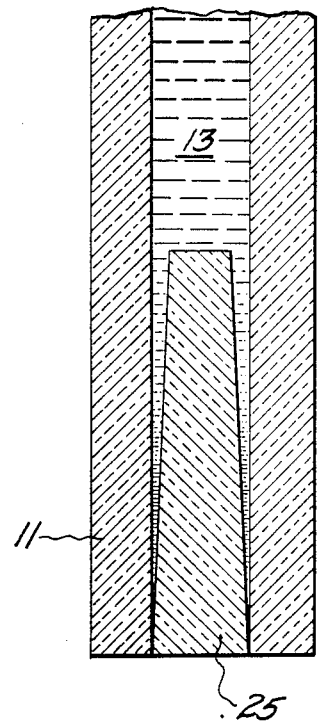

PROCESS FOR PREPARING A SINTERED CERAMIC ARTICLE WITH POROUS REGION

This application is a division, of application Ser. No. 451,501, filed Dec. 20, 1982, U.S. Pat. No. 4,560,413.

This invention is directed to useful articles of sintered metallic oxide and, in particular, to the provision of porous regions in otherwise non-porous bodies. One such useful article described herein is the housing for a reference electrode for high temperature aqueous systems.

DESCRIPTION OF THE INVENTION

A sintered metallic oxide article is disclosed comprising a non-porous body having at least one porous region formed therein in the general shape of a hollow cylinder, said region placing opposite sides of the body in flow communication. A method is set forth for producing the porous region with a preselected effective open cross-sectional area.

BRIEF DESCRIPTION OF THE DRAWING

The features of this invention believed to be novel and unobvious over the prior art are set forth with particularity in the appended claims. The invention itself, however, as to the organization, method of operation and objects and advantages thereof, may best be understood by reference to the following description taken in conjunction with the accompanying drawing wherein:

FIG. 1 is a view in section through a reference electrode employing a sintered metallic oxide housing constructed according to one embodiment of this invention and FIG. 2 is an enlarged view in section of the end of an electrode housing with a tapered plug inserted according to the preferred process prior to firing.

MANNER AND PROCESS OF MAKING AND USING THE INVENTION

The invention is described herein in connection with the construction of a one-piece ceramic housing for a silver/silver chloride reference electrode suitable for use in measurements in high-temperature, high-pressure aqueous environments. Conventional reference electrodes, such as those described by Vermilyea and Indig [*J. Electrochem. Soc.*, Vol. 119, page 39 (1972)] employ a tetrafluoroethylene housing and, therefore, are susceptible to rapid hydrogen permeation. Tests of a reference electrode configuration employing the one-piece housing of FIG. 1 indicate that this construction operates well both in static and flowing systems at temperatures and pressures up to at least 290° C. and 1500 psi in the presence of hydrogen.

In order to accommodate operation at such high temperatures, it is necessary that provision be made for the escape of more than 25 percent of the electrolyte solution contained in the electrode housing at 25° C. before the system can equilibrate at about 290° C. This is accomplished with the microporous junction of preselected effective cross-sectional area according to this invention.

Referring to FIG. 1, the reference electrode 10 comprises longitudinally-extending tubular housing 11 of sintered zirconia having electrode 12 suspended therein. Housing 11 is referred to as being "one-piece", because the tubular portion thereof is sintered, albeit imperfectly, to the close fitting plug 21. Electrode 12 is made of high purity silver with the lower end thereof (shown darkened) coated with silver chloride and immersed in a potassium chloride electrolyte solution 13. The upper end of ceramic housing 11 is provided with sealing member 14 made of tetrafluoroethylene containing 40 percent by weight zirconia in order to reduce expansion and distortion at high temperatures. Electrical isolation of electrode 12 is completed with ceramic member 16, which biases member 14 into sealing engagement by the application of pressure thereto by threaded fitting 17. Threaded connection 18 accommodates installation of the reference electrode 10 through the wall of an enclosure containing an aqueous system in which measurements (e.g. pH) are to be made.

The use of a reference electrode employing a glass housing for the measurement of pH is illustrated in U.S. Pat. No. 4,264,424—Niedrach. The pH sensing membrane of the Niedrach hydrogen ion sensor is made of an oxygen ion conducting ceramic, such as stabilized zirconia. The Niedrach patent is incorporated by reference. Various compositions of metallic oxide powder are described in U.S. Pat. No. 3,429,962—Krystyniak. In the practice of this invention the powders were consolidated into a body of the desired shape by isostatic pressing at 15,000 psi and the resulting body was then prefired at 1250° C. for one hour in air. The prefired metallic oxide body is provided with a through hole to be closed off, a prefired metallic oxide plug dimensioned to fit closely in this hole is inserted in one end of the hole and the resulting assembly is fired. This firing is accomplished in a hydrogen atmosphere at about 1900° C. The firing sinters the prefired metallic oxide members of this assembly rendering them non-porous. This provides a plug surrounded by and imperfectly sintered to the metallic oxide body. Thus, a microporous junction region is formed between the prefired metallic oxide members.

The preferred ceramic composition for the fabrication of housing 11 (which includes plug 21) employs 5 weight percent calcia as the stabilizing agent for the zirconia and 2 weight percent alumina is added. The alumina enhances liquid phase sintering of the metallic oxides and eliminates connected porosity. Any alumina on the external surfaces of the sintered housing is leached out upon exposure to water at 288° C. leaving a very stable, inert, non-porous and (at 288° C.) electrically insulating structure. In some instances the connected porosity extends to the outer surface to a sufficient extent to enable use of the housing without further modification. In those instances in which the flow communication characteristics of the annulus are such that there is insufficient porosity to accommodate the significant changes in aqueous solution density at the operating temperature, which require that solution be able to escape from within the electrolyte chamber, this can be readily accommodated by sequentially cutting thin slices (e.g. each approximately 0.1 inch thick) from the end of the unified tubular portion of housing 11 and close fitting plug 21 imperfectly sintered thereto. By this expedient the connected porosity between the inside and outside of the housing via the porous annulus can be increased. A simple test to determine whether or not the extent of porosity has been reached to the desired extent is to apply a gas (e.g. nitrogen) under pressure of about 10 psi to the interior of the housing and observe the extent of bubble formation in a thin film of water on the outer surface of the annulus.

An indication of the effective open cross-sectional area of the porous annulus can be determined by the use of electrical impedance measurements at constant temperature. Thus, such measurements have been made with housing 11 resting with its tip at the bottom of a stainless steel beaker filled with an aqueous solution containing 0.1 molar KCl to the same level as an identical solution in the electrolyte chamber within housing 11. The valve of electrical resistance between the beaker and a platinum wire touching plug 21 at its inner surface was used to calculate the cross-sectional area and diameter of an equivalent round hole the length of the plug. Examples of the results of such impedance measurements are shown in Table 1. Among the symbols employed: $\rho$ is resistivity (ohm cm) and $\kappa$ is the conductivity of the KCl.

TABLE 1

IMPEDANCE MEASUREMENTS ON ZIRCONIA REFERENCE ELECTRODE HOUSINGS

| | Plug Length (mm) | Resistance (k$\Omega$)[1] | A (cm$^2$)[2] | d ($\mu$m)[3] |
|---|---|---|---|---|
| 1 | 4.0 ± .05 | 77.0 ± 0.05 | 4.25 × 10$^{-4}$ | 233 |
| 2 | 2.5 | 200 ± 2 | 1.04 × 10$^{-4}$ | 115 |
| 3 | 1.8 | 270 ± 10 | 0.54 × 10$^{-4}$ | 83 |
| 4 | 2.0 | 250 ± 30 | 0.66 × 10$^{-4}$ | 92 |

[1] 0.1 m KCl, 1000 Hz, 21.8° C., 1.21 × 10$^{-2}$ ohm$^{-1}$ cm$^{-1}$
[2] R = $\rho$l/A, A = l/R$\kappa$ for a uniform cross section A, length l
[3] d = (4A/$\pi$)$^{\frac{1}{2}}$, the diameter of a round cylinder with cross section A.

The accuracy of the measurements made in this way depends upon complete filling of the continuous porosity in the annular region. Characterization by gas flow is simpler and quicker.

FIG. 2 shows a preferred embodiment of this invention. Instead of employing a prefired metallic oxide plug machined in the form of a right circular cylinder, plug 25 is provided with a slight taper (greatly accentuated in the drawing). In the same manner as described hereinabove, the plug is fitted into the uniform bore of tube 11 before the ceramic is fired to final dimensions. The fired assembly possesses a porous annulus having a substantially uniform gradation of porosity. Thus, successive thin slices taken from the tip of tube 11 expose more and more inperfectly sintered regions in the annulus assuring selectivity of the desired porosity in the finished product.

Although this invention has been illustrated by describing the manner of preparation of a porous region in the shape of a hollow cylinder, the invention is equally applicable to the preparation of other geometric shapes providing preselected porosity through sintered otherwise non-porous metallic oxide walls or bodies. An example of a use for a sintered metallic oxide enclosure provided with a plurality of such porous regions would be as a sparger for the introduction of a gas into surrounding liquid. The invention, of course, is not limited to any particular metallic oxide or mixtures of metallic oxide.

What we claim as new and desire to secure by Letters Patent of the United States is:

1. A process for the manufacture of a sintered metallic oxide article comprising a non-porous body having a cylindrically shaped hole and a close-fitting, non-porous plug at one end of said shaped hole and at least one porous region in the general shape of a hollow cylinder intermediate said cylindrically shaped hole and said plug, said process comprising the steps of:
   (a) providing a metallic oxide body prefired at about 1250° C. for about one hour in air in a preselected shape having juxtaposed surfaces,
   (b) providing a cylindrically-shaped hole through said body connecting said surfaces,
   (c) introducing a close-fitting plug of metallic oxide prefired at about 1250° C. for about one hour in air into said hole to produce an assembly, and
   (d) sintering said assembly in a hydrogen atmosphere at about 1900° C. to render said body and said plug non-porous and to form a microporous junction therebetween in the general shape of a hollow cylinder.

2. The process of claim 1 including the additional step of removing material from an exterior surface of said microporous junction and said non-porous body until the effective open cross-sectional area of said junction reaches a preselected value.

3. The process of claim 1 wherein the metallic oxide of both said body and said plug is stabilized zirconia.

* * * * *

UNITED STATES PATENT AND TRADEMARK OFFICE
CERTIFICATE OF CORRECTION

PATENT NO. : 4,576,667

DATED : March 18, 1986

INVENTOR(S) : Dale F. Taylor and Louis S. Sammler

It is certified that error appears in the above-identified patent and that said Letters Patent is hereby corrected as shown below:

Front page: Related U.S. Application Data: Change "Pat. No. 4,560,413" to --Pat. No. 4,500,413--.
Column 1, line 6, change "4,560,413" to --4,500,413--.

Signed and Sealed this

Nineteenth Day of August 1986

[SEAL]

Attest:

DONALD J. QUIGG

Attesting Officer

Commissioner of Patents and Trademarks